United States Patent [19]

Hirai et al.

[11] Patent Number: 5,612,289

[45] Date of Patent: Mar. 18, 1997

[54] 4-IMINO-OXAZOLIDINE-2-ONE DERIVATIVES, A PROCESS FOR PRODUCING SUCH DERIVATIVES AND A HERBICIDE CONTAINING THEM AS AN ACTIVE INGREDIENT

[75] Inventors: Kenji Hirai; Tomoko Matsukawa; Tomoyuki Yano; Katsuyuki Masuda, all of Kanagawa-ken; Tomoko Yoshii, Shizuoka-ken; Takehito Mouri, Chiba-ken; Sadayuki Ugai; Osamu Yamada, both of Shizuoka-ken, all of Japan

[73] Assignees: Sagami Chemical Research Center; Kaken Pharmaceutical Co., Ltd., both of Japan

[21] Appl. No.: 624,557

[22] PCT Filed: Oct. 7, 1994

[86] PCT No.: PCT/JP94/01683

§ 371 Date: Jul. 8, 1996

§ 102(e) Date: Jul. 8, 1996

[87] PCT Pub. No.: WO95/10509

PCT Pub. Date: Apr. 20, 1995

[30] Foreign Application Priority Data

Oct. 8, 1993 [JP] Japan ................... 5-276009

[51] Int. Cl.⁶ ............... A01N 43/76; C07D 263/48; C07D 263/44
[52] U.S. Cl. ............... 504/270; 548/230; 548/226
[58] Field of Search ............... 548/230, 226; 504/270

[56] References Cited

U.S. PATENT DOCUMENTS

| | | | |
|---|---|---|---|
| 3,671,535 | 6/1972 | Faidutti et al. | 548/230 |
| 3,703,526 | 11/1972 | Sato et al. | 548/230 |
| 3,743,651 | 7/1973 | Fujinam et al. | 548/230 |
| 4,818,272 | 4/1989 | Hirai et al. | 504/270 |
| 5,100,457 | 3/1992 | Hirai et al. | 504/270 |

*Primary Examiner*—Fiona T. Powers
*Attorney, Agent, or Firm*—Nixon & Vanderhye

[57] ABSTRACT

The invention relates to 4-imino-oxazolidine-2-one derivatives represented by the general formula (1):

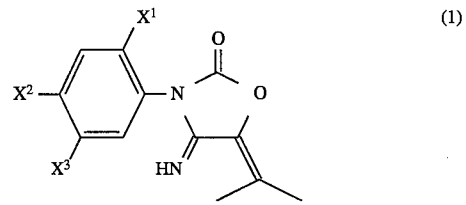

and a process for producing said compounds by reacting aryl isocyanates of the general formula (2):

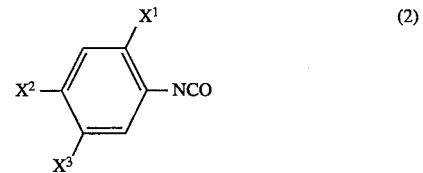

with methacrolein cyanohydrin in the presence of a base, as well as a herbicide containing said compounds as an active ingredient; it also relates to a process for producing oxazolidinedione derivatives useful as herbicides by hydrolyzing said compounds.

11 Claims, No Drawings

4-IMINO-OXAZOLIDINE-2-ONE DERIVATIVES, A PROCESS FOR PRODUCING SUCH DERIVATIVES AND A HERBICIDE CONTAINING THEM AS AN ACTIVE INGREDIENT

TECHNICAL FIELD

The present invention relates to 4-imino-oxazolidine-2-one derivatives represented by the General formula (1):

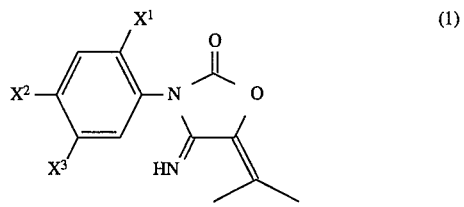

(where $X^1$ is a hydrogen atom or a halogen atom; $X^2$ is a hydrogen atom, a halogen atom or an alkyloxy group, preferably having 1–6 carbon atoms; $X^3$ is a hydrogen atom, a halogen atom, an alkyloxy group, preferably having 1–6 carbon atoms, a cycloalkyloxy group, preferably having 3–6 carbon atoms, or an alkynyloxy group, preferably having 3–4 carbon atoms) or salts thereof, a process for producing such derivatives or salts thereof, and a herbicide containing such derivatives or salts thereof as an active ingredient. The present invention also relates to a process for producing oxazolidinedione derivatives of the general formula (3) by hydrolyzing the imino group in position 4 of 4-imino-oxazolidine-2-one derivatives of the general formula (1) as follows:

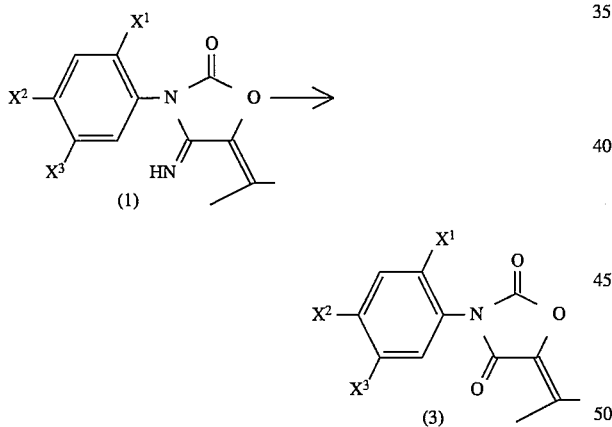

(were $X^1$, $X^2$ and $X^3$ each have the same meaning as defined above).

BACKGROUND ART

Conventionally, 4-imino-oxazolidine-2-one derivatives having substituted aryl groups on the nitrogen atom in position 3 are known to have fungicidal activity (see, for example, Japanese Patent Publication No. 43800/1972); however, there have been no reports on the synthesis of 4-imino-oxazolidine-2-one derivatives having an isopropylidene group in position 5 of the oxazolidine ring as represented by the general formula (1) in the present invention and it is entirely unknown that such derivatives have a potent herbicidal activity.

The 4-imino-oxazolidine-2-one derivatives described in Japanese Patent Publication No. 43800/1972 are produced by addition and cyclization reactions of the corresponding isocyanate and cyanoalcohol. However, no reaction has yet been known that employs a cyanoalcohol having a double bond in the a position and, what is more, the introduction of an isopropylidene group utilizing the isomerization of the double bond is a reaction that is a key to the synthesis of the 4-imino-oxazolidine-2-one derivatives of the present invention.

EP-0241559B teaches that oxazolidinedione derivatives represented by the general formula (3) are useful as the active ingredient of the herbicide it claims and such derivatives may be produced by subjecting an aryl isocyanate (2) to an addition cyclization reaction with a 2-hydroxy-3-methyl-3-butenoic acid ester (4) according to the scheme shown below. However, this process requires a two-step reaction for preparing the 2-hydroxy-3-methyl-3-butenoic acid ester which is used as a starting material and it is necessary to use many auxiliary materials; what is more, the desired product cannot necessarily be obtained with satisfactory yield.

Thus, the conventional method which uses the 2-hydroxy-3-methyl-3-butenoic acid esters (4) not only involves a prolonged reaction process but also requires the use of many auxiliary materials in association with the individual steps and these and the additional problem of low yield make the method economically disadvantageous for the production of oxazolidinedione derivatives of the general formula (3) which are useful as the active ingredient of herbicides. Hence, it is desired to develop a more efficient production process.

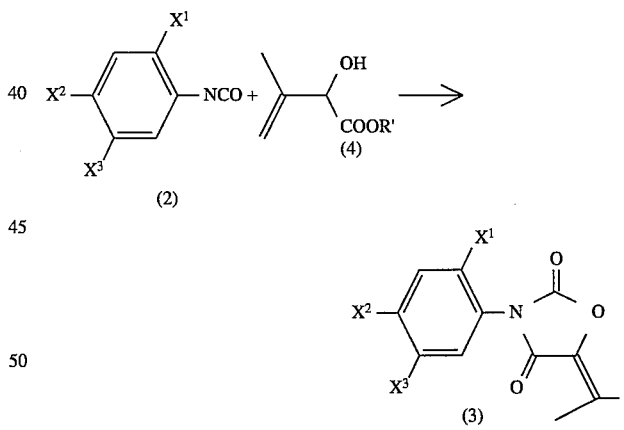

(where $X^1$, $X^2$ and $X^3$ each have the same meaning as defined above; R' is a lower alkyl group).

DISCLOSURE OF INVENTION

The present inventors conducted intensive studies with a view to solving the aforementioned problems of the prior art and found the following: the novel oxazolidine-2-one derivatives of the invention which are represented by the general formula (1) set forth above and which have an imino group in position 4 can be synthesized with high yield in a short process by reacting the aryl isocyanate which is an inexpensive starting material represented by the general formula (2) set forth above with methacrolein cyanohydrin (1-cyano-2-methyl-2-propen-1-ol) in the presence of a base; these compounds exhibit high herbicidal effects against major weeds in low-dose treatments while causing low injury to major crops, thereby assuring excellent performance as herbicides; by hydrolyzing these compounds, specifically at the imino group in position 4 under acidic conditions, oxazolidinedione derivatives of the general formula (3) can be produced more economically than in the conventional method. The present invention has been accomplished on the basis of these findings.

Thus, the present invention relates to 4-imino-oxazolidine-2-one derivatives represented by the general formula (1):

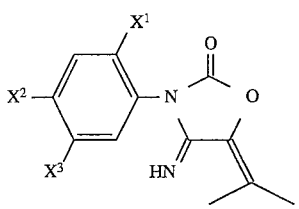

(1)

(where $X^1$, $X^2$ and $X^3$ each have the same meaning as defined above), and salts thereof.

The present invention also relates to a process for producing 4-imino-oxazolidine-2-one derivatives of the general formula (1):

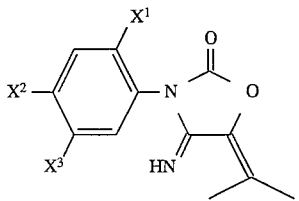

(1)

(where $X^1$, $X^2$ and $X^3$ each have the same meaning as defined above) by reacting an aryl isocyanate of the general formula (2):

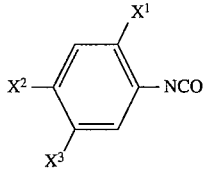

(2)

(where $X^1$, $X^2$ and $X^3$ each have the same meaning as defined above) with 1-cyano-2-methyl-2-propen-1-ol in the presence of a base.

The present invention also relates to a herbicide containing a 4-imino-oxazolidine-2-one derivative of the general formula (1):

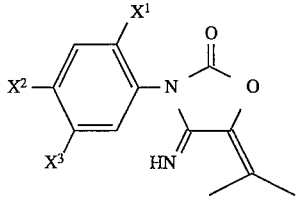

(1)

(where $X^1$, $X^2$ and $X^3$ each have the same meaning as defined above) or a salt thereof as an active ingredient.

The present invention further relates to a process for producing 5-isopropyliden-2,4-oxazolidinedione derivatives of the general formula (3):

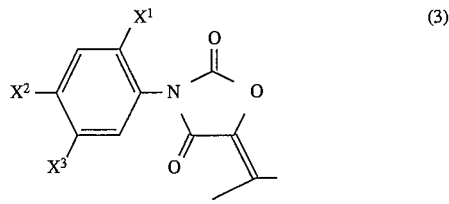

(3)

(where $X^1$, $X^2$ and $X^3$ each have the same meaning as defined above) by hydrolyzing 4-imino-oxazolidine-2-one derivatives of the general formula (1):

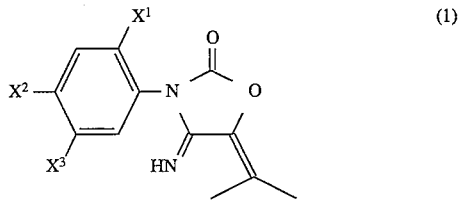

(1)

(where $X^1$, $X^2$ and $X^3$ each have the same meaning as defined above) under acidic conditions, as well as a process for producing 5-isopropyliden-2,4-oxazolidinedione derivatives of the general formula (3):

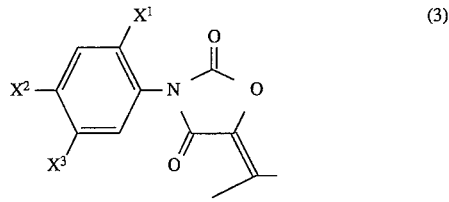

(3)

(where $X^1$, $X^2$ and $X^3$ each have the same meaning as defined above) by first reacting an aryl isocyanate of the general formula (2):

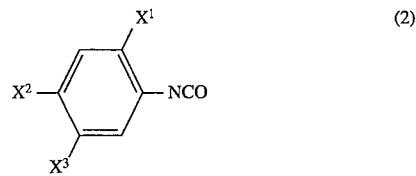

(2)

(where $X^1$, $X^2$ and $X^3$ each have the same meaning as defined above) with 1-cyano-2-methyl-2-propen-1-ol in the presence of a base and then hydrolyzing the imino group under acidic conditions.

The halogen atom represented by $X^1$, $X^2$ and $X^3$ in the 4-imino-oxazolidine-2-one derivatives of the general formula (1) which are the compounds of the present invention may be exemplified by a fluorine atom, a chlorine atom, a bromine atom, etc.

The alkyloxy group represented by $X^2$ or $X^3$ may be exemplified by a methoxy group, an ethoxy group, a propoxy group, an isopropoxy group, a butoxy group, an isobutoxy group, a pentyloxy group, a hexyloxy group, etc.

The cycloalkyloxy group represented by $X^3$ may be exemplified by a cyclopropyloxy group, a cyclopentyloxy group, a cyclohexyloxy group, etc. The alkynyloxy group may be exemplified by a propargyloxy group, a 1-butyn-3-yloxy group, a 2-butynyloxy group, etc.

Salts of the derivatives (1) may be exemplified hydrochlorides, sulfates, phosphates, etc.

If the aryl isocyanate represented by the general formula (2) which is to be used in the production process of the invention is not commercially available, it can be easily prepared by reacting the corresponding aniline derivative with a phosgene or an equivalent thereof in the usual manner. The corresponding aniline derivative can be prepared by reference to a conventional method such as the one described in Japanese Laid-Open Patent Application Nos. 17411/1993 or 43525/1993.

The 1-cyano-2-methyl-2-propen-1-ol can also be easily prepared by adding hydrocyanic acid to methacrolein (see Reference Examples 1 and 2 which follow).

The process of the present invention for producing 4-imino-oxazolidine-2-one derivatives requires that the aryl isocyanate (2) be reacted with the 1-cyano-2-methyl-2-propen-1-ol in the presence of a base. The base may be exemplified by organic amines such as triethylamine, tributylamine, N-methylmorpholine, pyridine and dimethylaniline, and alkali metal bases such as potassium carbonate, sodium carbonate, potassium hydrogencarbonate, sodium hydrogencarbonate, sodium hydride and sodium amide. The amount in which the base is to be used is not limited to any particular value and it may be a catalytic amount ranging from $1/100$–$1/10$ of the substrate for the reaction.

The addition cyclization reaction of interest may be performed in the absence of solvents but solvents that do no harm to the reaction may also be used, as exemplified by benzene, toluene, xylene, chlorobenzene, tetrahydrofuran, diethyl ether, diisopropyl ether, dimethoxyethane, hexane, octane, ethyl acetate, acetonitrile, acetone, N,N-dimethylformamide and N-methylpyrrolidone.

The process of generation of the 4-imino-oxazolidine-2-one derivatives (1) of the invention is shown by the following scheme: first, the hydroxyl group in 1-cyano-2-methyl-2-propen-1-ol is added to an isocyanato group to yield a carbamate derivative represented by the general formula (5); thereafter, the nitrogen in the amide is cyclized intramolecularly with the cyano group to form an intermediate (6) which, in turn, experiences a double bond shift to yield the 4-imino-oxazolidine-2-one derivative (1):

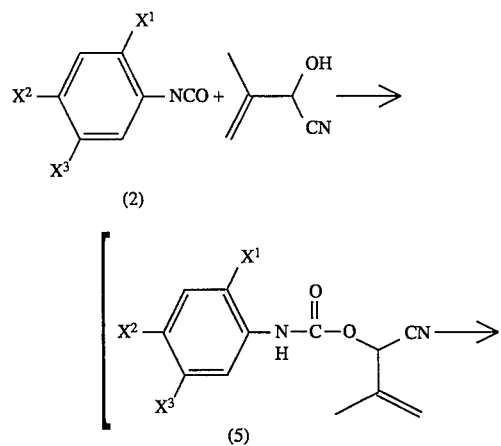

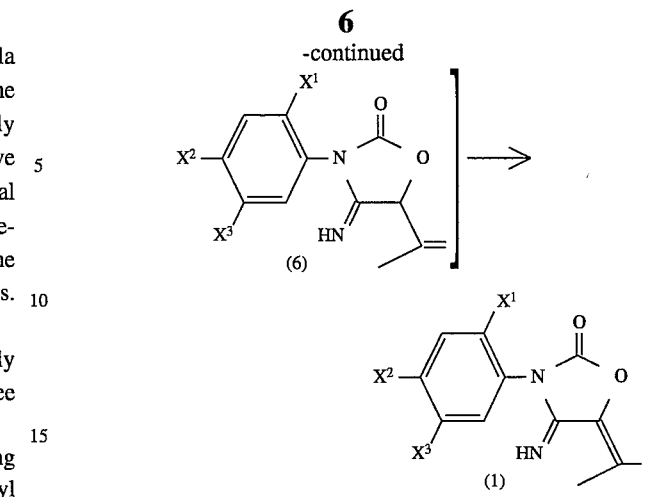

As for the temperature for the respective reactions, there is no need for heating in the reaction of adding 1-cyano-2-methyl-2-propen-1-ol to the active aryl isocyanate (2) and the reaction will proceed satisfactorily under low temperatures below room temperature. The subsequent intramolecular cyclization reaction is also believed to be a very rapid reaction from a standpoint of chemical kinetics and hence will proceed at room temperature; however, this reaction can be completed within a short time by performing it under heating at 30°–110° C., preferably about 40°–80° C. The reaction for the shift of a double bond is believed to a thermodynamically controlled reaction and the rate of the reaction can be increased by performing it under heating; the reaction can be brought to a complete end by performing it under heating ranging from room temperature to 150° C., preferably from about 60° to 110° C.

Thus, the production process of the invention yields the desired product by three different elementary reactions via the carbamate derivative (5) and the intermediate (6). In the process, these reactions are allowed to proceed sequentially under appropriate conditions, whereby the end product 4-imino-oxazolidine-2-one derivative (1) can be obtained through one point without isolating the intermediates (5) and (6).

After completion of the reaction, the 4-imino-oxazolidine-2-one derivative (1) can be obtained by usual procedures. If desired, conc. HCl may be added to the obtained 4-imino-oxazolidine-2-one derivative (1) in solution, for example, in toluene so that the derivative is isolated as a hydrochloride. Needless to say, chemically acceptable other salts such as sulfates and phosphates are also included within the scope of the invention.

The thus obtained 4-imino-oxazolidine-2-one derivatives (1) may have the imino group in position 4-hydrolyzed to a carbonyl group under acidic conditions, whereby they can be easily converted to oxazolidinedione derivatives (3).

The hydrolytic reaction may be performed either by heating with 1–12N HCl being added to the 4-imino-oxazolidine-2-one derivative (1) or by heating with 1–12N HCl being added to the 4-imino-oxazolidine-2-one derivative (1) as it is dissolved in an organic solvent, so that the desired oxazolidinedione derivative (3) can be produced.

The acid that can be used in the reaction may be exemplified by hydrochloric acid, sulfuric acid, phosphoric acid and other mineral acids and it is preferred to use hydrochloric acid which is comparatively safe, easy to handle and inexpensive. Any organic solvents are usable as long as they are stable under acidic conditions and will do no harm to the reaction and they may be exemplified by benzene, toluene, xylene, chlorobenzene, tetrahydrofuran, diethyl ether, diisopropyl ether, dimethoxyethane, ethyl acetate, acetonitrile, acetone, methanol, ethanol, etc.

The reaction may proceed at room temperature but if it is carried out under heating, the reaction is completed within a short time to give the desired product with high yield; hence, the reaction is preferably carried out under heating at about 60°–150° C.

It should also be noted that in the production of the oxazolidinedione derivatives (3), there is no need to isolate the 4-imino-oxazolidine-2-one derivatives (1) and after the addition cyclization reaction between the aryl isocyanate (2) and 1-cyano-2-methyl-2-propen-1-ol, an acid may be added to the reaction solution, which is hydrolyzed by heating under reflux to produce the oxazolidinedione derivatives (3).

The reactions at issue may be carried out successively under the respective appropriate reaction conditions using the solvents and acids exemplified in connection with the already described production of the 4-imino forms (1) and the reaction for their hydrolysis and this procedure is preferred since the desired product can be obtained with high yield.

The compounds of the present invention, when applied in soil and foliage treatments on non-ricefields, show excellent herbicidal effects in low-dose treatments against various noxious weeds including broadleaf weeds such as *Chenopodium album, Amaranthus viridis, Abutilon theophrasti* and *Stellaria media*, and gramineous weeds such as *Echinochloa crusgalli* and *Setaria viridis* and yet cause no significant injury to major crops including broadleaf crops such as soybean and cotton and gramineous crops such as corn. The compounds also show excellent effects in low-dose treatments against various noxious weeds in ricefields including gramineous weeds such as *Echinochloa oryzicola*, broadleaf weeds such as *Lindernia pyxidaria, Rotala indica* and *Elatine triandra* and sedge weeds such as *Scirpus juncoides* and *Eleocharis acicularis* and yet cause very slight injury to transplanted rice.

BEST MODE FOR CARRYING OUT THE INVENTION

The following Examples, Reference Examples and Test Examples are provided for further illustrating the present invention but are in no way to be taken as limiting.

EXAMPLE 1

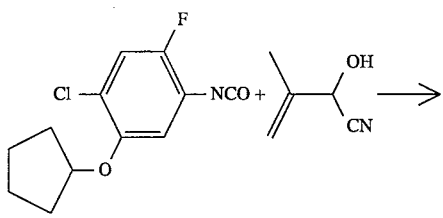

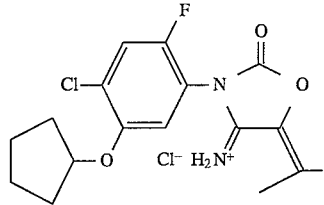

A round-bottomed flask (500 cc) equipped with a dropping funnel was charged with 4-chloro-5-cyclopentyloxy-2-fluorophenyl isocyanate (50.0 g, 0.196 mol) and triethylamine (1.0 mL), as well as isopropyl ether (100 mL) and methacrolein cyanohydrin (15.0 g, 0.155 mol) was dropwise added slowly with stirring under cooling in an ice-water bath. After the addition, the mixture was heated to room temperature and stirred at 50° C. for an additional 2 h. After completion of the reaction, the precipitating crystal was recovered by filtration, washed with hexane and dried to give 3-(4-chloro-5-cyclopentyloxy-2-fluorophenyl)-4-imino-5-isopropylideneoxazolidine-2-one as a pale yellow crystal (45.3 g; yield, 65.6%).

MP:131°–133° C.

$^1$H-NMR(400 MHz, CDCl$_3$, TMS, ppm): δ1.64(2H, m), 1.89(6H, m), 2.03(3H, s), 2.30(3H, s), 4.74(1H, m), 6.82(1H, d, $J_{HF}$=5.15 Hz), 7.35(1H, d, $J_{HF}$=8.84 Hz).

IR(KBr disk, cm$^{-1}$): 2950, 1790, 1670, 1500, 1430, 1380, 1310, 1290, 1230, 1190, 1130, 1050, 830, 750.

MS(m/e, relative intensity): 355(M$^+$+3, 1.40), 354(M$^+$+2, 4.54), 353(M$^+$+1, 3.80), 352(M$^+$, 13.74), 286(31.65), 284(90.37), 189(32.39), 188(12.16), 187(100), 158(3.73), 70(82.44), 69(24.54), 42(34.86), 41(84.61), 39(22.51), 28(14.20), 18(19.36).

EA (%, calcd. for C$_{17}$H$_{18}$ClFN$_2$O$_3$): C; 57.86(57.87), H; 5.16(5.15), N; 7.75(7.94).

The resulting 3-(4-chloro-5-cyclopentyloxy-2-fluorophenyl)-4-imino-5-isopropylideneoxazolidine-2-one was dissolved in toluene and conc. HCl (ca. 2 eq.) was added to the solution at room temperature; the mixture was stirred thoroughly and the resulting white solids was subjected to filtration, washed thoroughly with toluene and hexane and subsequently dried to yield 3-(4-chloro-5-cyclopentyloxy-2-fluorophenyl)-4-imino-5-isopropylideneoxazolidine-2-one hydrochloride (compound 1) almost quantitatively.

MP:134°–135° C.

$^1$H-NMR(400 MHz, DMSO$_6$+D$_2$O, TMS, ppm): δ1.72(2H, m), 1.74(4H,m), 1.89(2H, m), 2.22(3H, s), 2.25(3H, s), 4.76(1H, m), 7.34(1H, d, $J_{HF}$=4.19 Hz ), 7.36(1H, d, $J_{HF}$=4.26 Hz).

IR(KBr disk, cm$^{-1}$): 2950, 1820, 1630, 1500, 1460, 1390, 1280, 1180, 1140, 1050, 860, 750, 720.

EXAMPLE 2

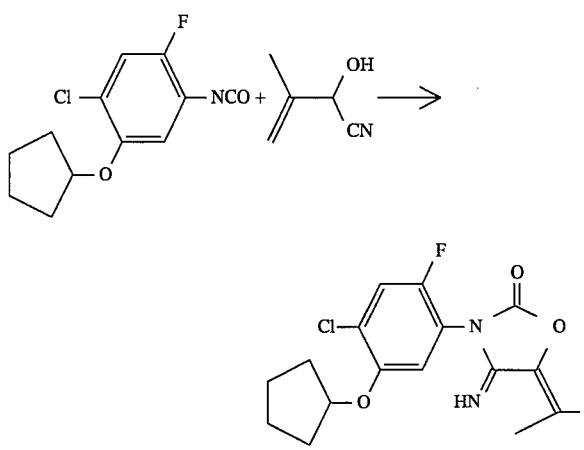

A round-bottomed flask (500 cc) equipped with a mechanical stirrer and a dropping funnel was charged with 4-chloro-5-cyclopentyloxy-2-fluorophenyl isocyanate (100 g, 0.392 mol) and toluene (100 mL) and, subsequently, a solution of methacrolein cyanohydrin (35.0 g, 0.360 mol) and triethylamine (1.0 mL) in toluene (50 mL) was dropwise added slowly over 15 min with stirring under cooling in an ice-water-bath. After the addition, the mixture was heated to room temperature and stirred at room temperature for an additional 4 h, followed by washing with aqueous 1N sodium hydroxide (50 mL×2), 1N HCl (50 mL×2) and water (50 mL×2) and drying with anhydrous magnesium sulfate. After removing the desiccant, the solvent was distilled off under vacuum to give a brown crude product (124.5 g). A small amount of hexane was added to the crude product and the precipitating crystal was recovered by filtration, washed with hexane and subsequently dried to give 3-(4-chloro-5-cyclopentyloxy-2-fluorophenyl)-4-imino-5-isopropylideneoxazolidine-2-one (compound 2) as a pale yellow crystal (primary crystal; 53.9 g; yield, 39.0%).

EXAMPLE 3

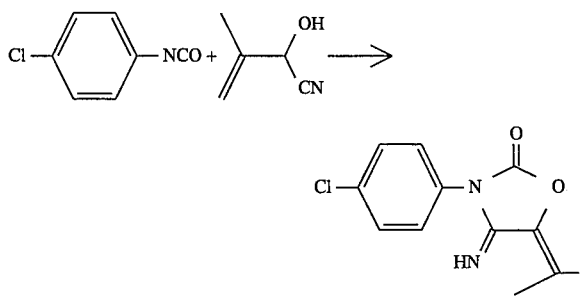

A round-bottomed flask (200 cc) equipped with a dropping funnel was charged with 4-chlorophenyl isocyanate (11.3 g, 73.7 mmol) and triethylamine (0.5 mL), as well as isopropyl ether (40 mL) and toluene (30 mL) and methacrolein cyanohydrin (8.94 g, 92.1 mmol) was dropwise added slowly with stirring at room temperature. After the addition, the mixture was stirred at room temperature for an additional 12 h. After completion of the reaction, the precipitating solids was recovered by filtration, washed with ether (5 mL×2) and hexane (5 mL×2) and subsequently dried to give 3-(4-chlorophenyl)-4-imino-5-isopropylideneoxazolidine-2-one (compound 3) as a white crystal (7.40 g; yield, 40.1%).

MP: 153°–155° C.

$^1$H-NMR(400 MHz, CDCl$_3$, TMS, ppm): δ2.02(3H, s), 2.31(3H, s), 7.26(2H, d, J=8.66 Hz), 7.46(1H, br s), 8.57(2H, d, J=8.57 Hz).

IR(Kbr disk, cm$^{-1}$): 3250, 1770, 1660, 1490, 1410, 1290, 1260, 1200, 1140, 1090, 1005, 840, 830, 750, 510.

MS(M/e, relative intensity): 253(M$^+$+3, 2.66), 252(M$^+$+2, 16.69), 251(M$^+$+1, 7.40), 250(M$^+$, 51.20), 155(21.93), 154(7.13), 153(67.75), 125(16.78), 90(15.17), 70(100.0), 42(36.82), 41(25.73), 39(18.00), 18(13.83).

EA(%, calcd. for C$_{12}$H$_{11}$ClN$_2$O$_2$): C; 57.65(57.49), H; 4.22(4.43), N; 11.34(11.18).

EXAMPLE 4

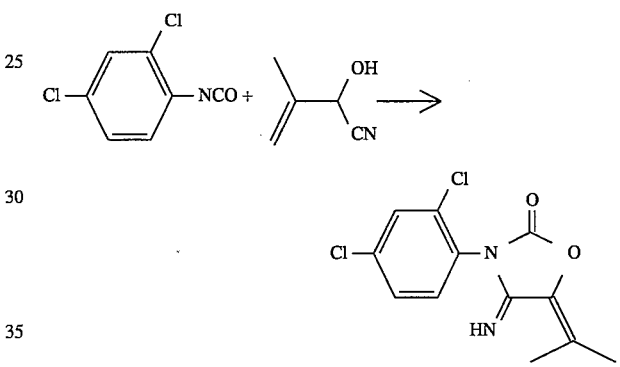

A round-bottomed flask (100 cc) equipped with a dropping funnel was charged with 2,4-dichlorophenyl isocyanate (2.66 g, 14.2 mmol) and triethylamine (0.25 mL), as well as toluene (20 mL) and methacrolein cyanohydrin (2.43 g, 25.0 mmol) was dropwise added slowly with stirring under cooling in an ice-water bath. After the addition, the mixture was heated to room temperature and stirred at 50° C. for an additional 30 min. After completion of the reaction, the reaction mixture was washed with aqueous 1N sodium hydroxide (20 mL×2) and 1N HCl (30 mL) and dried with magnesium sulfate; thereafter, the solvent was distilled off under vacuum to yield a crude product, which was recrystallized from toluene/hexane to give 3-(2,4-dichlorophenyl)-4-imino-5-isopropylideneoxazolidine-2-one (compound 4) as a white crystal (1.92 g; yield, 47.4%).

MP: 129°–130° C.

$^1$H-NMR(400 MHz, CDCl$_3$, TMS, ppm): δ2.03(3H, s), 2.28(3H, s), 7.00–7.70(1H, br s), 7.29(1H, d, J=8.47 Hz), 7.44(1H, dd, J=8.47 Hz and 2.25 Hz), 7.63(1H, d, J=2.25 Hz).

IR(KBr disk, cm$^{-1}$): 3360, 1780, 1660, 1490, 1410, 1280, 1210, 1135, 1090, 1070, 1000, 820, 750, 740.

MS(m/e, relative intensity): 288(M$^+$+3, 3.08), 287(M$^+$+2, 3.15), 286(M$^+$+1, 17.47), 285(M$^+$, 5.03), 284(26.42), 189(18.59), 187(28.65), 124(9.81), 70(100.0), 42(45.98), 41(28.65), 39(15.97), 18(17.89).

EA(%, calcd for $C_{12}H_{10}Cl_2N_2O_2 \cdot 1/4H_2O$): C; 49.80(49.76), H; 3.36(3.66), N; 9.54(9.67).

EXAMPLE 5

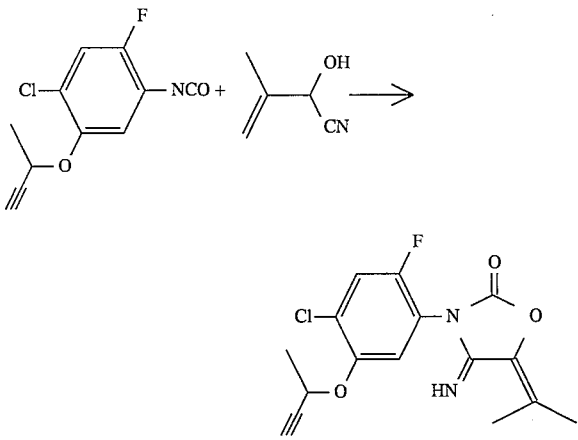

A round-bottomed flask (300 cc) equipped with a dropping funnel was charged with 5-(1-methyl-2-propynyloxy)-4-chloro-2-fluorophenyl isocyanate (10.0 g, 41.7 mmol) and triethylamine (1.0 mL), as well as isopropyl ether (40 mL) and diethyl ether (50 mL) and methacrolein cyanohydrin (4.86 g, 50.0 mmol) was dropwise added slowly with stirring under cooling in an ice-water bath. After the addition, the mixture was heated to room temperature and stirred for an additional 12 h. After completion of the reaction, the reaction mixture was poured into 1N HCl (50 mL) and extraction was conducted with ethyl acetate (50 mL×3). The organic layer was dried with magnesium sulfate and the solvent was subsequently distilled off under vacuum to yield a crude product, which was purified by silica gel column chromatography (eluting solvents: ethyl acetate/hexane=1/5). The separated product of interest in turn was recrystallized from ether/hexane to give 3-[5-(1-methyl-2-propynyloxy)-4-chloro-2-fluorophenyl]-4-imino-5-isopropylideneoxazolidine-2-one (compound 5) as a white crystal (7.37 g; yield, 52.4%).

Mp: 114°–115° C.

$^1$H-NMR(400 MHz, CDCl$_3$, TMS, ppm): δ1.74(3H, d, J=6.57 Hz), 2.03(3H, s), 2.29(3H, s), 2.57(1H, d, J=2.04 Hz), 4.84(1H, dq, J=6.57 Hz and 2.04 Hz), 7.35(1H, d, J$_{HF}$=6.20 Hz), 7.38(1H, d, J$_{HF}$=8.95 Hz)

IR(KBr disk, cm$^{-1}$): 3300, 3200, 2100, 1800, 1675, 1505, 1430, 1385, 1305, 1285, 1235, 1190, 1140, 1105, 1090, 1050, 1025, 870, 830, 750.

MS(m/e, relative intensity): 339(M$^+$+3, 1.84), 338(M$^+$+2, 9.74), 337(M$^+$+1, 6.03), 336(M$^+$, 28.62), 286(6.29), 285(7.69), 284(18.61), 283(16.55), 189(12.19), 188(5.30), 187(36.63), 158(2.27), 70(100.0), 69(19.09), 53(60.17), 42(54.76), 41(40.15), 27(40.27), 18(18.16).

EA(%, calcd. for $C_{16}H_{14}ClFN_2O_3$): C; 56.81(57.06), H; 4.02(4.20), N; 8.42(8.32).

EXAMPLE 6

A round-bottomed flask (200 cc) equipped with a dropping funnel was charged with 4-methoxyphenyl isocyanate (4.84 g, 32.5 mmol) and triethylamine (0.5 mL), as well as isopropyl ether (30 mL) and methacrolein cyanohydrin (4.50 g, 46.3 mmol) was dropwise added slowly with stirring at room temperature. After the addition, the mixture was stirred at room temperature for 12 h. After completion of the reaction, the reaction mixture was concentrated under vacuum to yield a crude product, which was purified by silica gel column chromatography (eluting solvents: ethyl acetate/hexane=1/5). The separated product of interest in turn was recrystallized from ether/hexane to give 3-(4-methoxyphenyl)-4-imino-5-isopropylideneoxazolidine-2-one (compound 6) as a white crystal (3.32 g; yield, 41.5%).

MP:119°–121° C.

$^1$H-NMR(400 MHz, CDCl$_3$, TMS, ppm): δ2.02(3H, s), 2.30(3H, s), 3.86(3H, s), 7.05(2H, d, J=8.91 Hz), 7.21(2H, d, J=7.94 Hz, 7.39(1H, br s).

IR(KBr disk, cm$^{-1}$): 3250, 2950, 1780, 1660, 1510, 1435, 1400, 1290, 1250, 1200, 1140, 1110, 1015, 870, 840, 755, 610.

MS(m/e, relative intensity): 247(M$^+$+1, 12.55), 246(M$^+$, 67.87), 218(3.52), 150(14.86), 149(100.00), 134(17.27), 106(7.64), 78(7.93), 70(56.39), 42(27.87), 41(17.90), 28(10.76), 18(18.61).

EA(%, calcd. for $C_{13}H_{14}N_2O_3$): C; 63.66(63.39), H; 5.72(5.74), N; 11.37(11.38).

EXAMPLE 7

A round-bottomed flask (100 cc) equipped with a dropping funnel was charged with 3,4-dichlorophenyl isocyanate (1.41 g, 7.47 mmol) and triethylamine (0.2 mL), as well as toluene (15 mL) and methacrolein cyanohydrin (0.907 g, 9.34 mmol) was dropwise added slowly with stirring at room temperature. After the addition, the mixture was stirred at room temperature for 12 h. After completion of the reaction, the precipitating solids was filtered off and thereafter the filtrate was washed with aqueous 1N sodium hydroxide (5 ml), a saturated aqueous solution of sodium hydrogensulfite (5 ml) and 1N HCl (5 ml). The organic layer was dried with magnesium sulfate and thereafter the solvent was distilled off under vacuum to yield a crude product, which was recrystallized from toluene/hexane to give 3-(3,4-dichlorophenyl)-4-imino-5-isopropylideneoxazolidine-2-one (compound 7) as a white crystal (0.820 g; yield, 38.6%).

MP: 132°–134° C.

$^1$H-NMR(400 MHz, CDCl$_3$, TMS, ppm): δ2.03(3H, s), 2.31(3H, s), 7.15(1H, br s), 7.28(1H, d, J=8.47 Hz), 7.45(1H, dd, J=8.47 Hz and 2.27 Hz), 7.65(1H, d, J=2.27 Hz).

IR(KBr disk, cm$^{-1}$): 3350, 3050, 1780, 1660, 1490, 1410, 1380, 1280, 1210, 1135, 1090, 1065, 1000, 820, 780, 755, 740, 680.

MS(m/e, relative intensity): 288(M$^+$+3, 3.67), 287(M$^+$+2, 3.03), 286(M$^+$+1, 20.23), 285(M$^+$, 5.21), 284(31.62), 189(25.66), 187(39.97), 124(13.43), 70(100), 42(37.55), 41(25.81), 18(32.43).

EA(%), calcd. for C$_{12}$H$_{10}$Cl$_2$N$_2$O$_2$.1/4H$_2$O): C; 49.89(49.76), H; 3.50(3.66), N; 9.67(9.55).

EXAMPLE 8

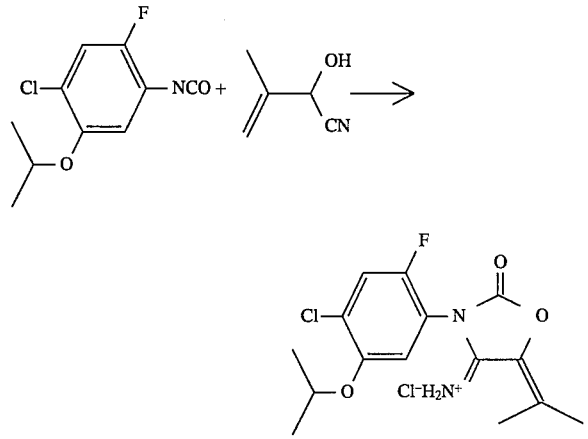

A round-bottomed flask (100 cc) equipped with a dropping funnel was charged with 4-chloro-2-fluoro-5-isopropyloxyphenyl isocyanate (2.30 g, 10.0 mmol) and triethylamine (0.1 mL), as well as toluene (10 mL) and methacrolein cyanohydrin (1.07 g, 11.0 mmol) was dropwise added slowly under stirring at room temperature. After the addition, the mixture was stirred at 80° C. for 2 h. After completion of the reaction, the reaction mixture was concentrated under vacuum and the resulting crude product was purified by silica gel column chromatography (eluting solvents: ethyl acetate/hexane=1/5) to yield 3-(4-chloro-2-fluoro-5-isopropyloxyphenyl)-4-imino-5-isopropylideneoxazolidine-2-one as a yellow oil (1.69 g). Subsequently, the imino form was dissolved in toluene (20 mL) under cooling with ice and 12N HCl (1 mL) was added. A white hydrochloride immediately formed and it was recovered by filtration to give the desired product (compound 8) as white solids (0.881 g; yield, 26.9%).

MP: 201°–203° C.

$^1$H-NMR(400 MHz, CDCl$_3$, DMSO-d$_6$): δ1.31(6H, d, J=5.93 Hz), 2.06(3H, s), 2.30(3H, s), 4.53(1H, p, J=5.93 Hz), 7.54(1H, d, J$_{HF}$=6.68 Hz), 7.79(1H, d, J$_{HF}$=9.39 Hz), 9.24(2H, br s).

IR(KBr disk, cm$^{-1}$): 3042, 2984, 2936, 2558, 2473, 1831, 1651, 1543, 1507, 1470, 1391, 1215, 1186, 1146, 1109, 1051, 851.

EXAMPLE 9

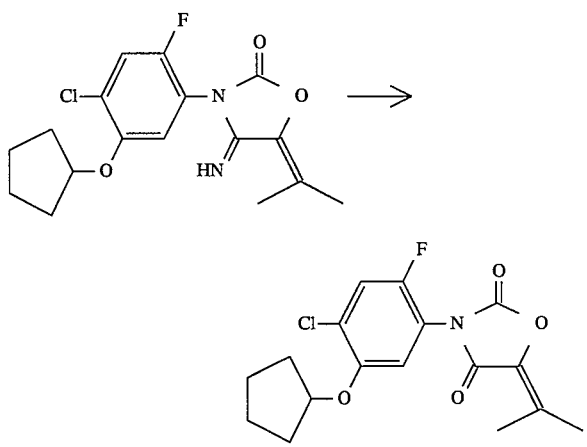

A round-bottomed flask (300 cc) was charged with 3-(4-chloro-5-cyclopentyloxy-2-fluorophenyl)-4-imino-5-isopropylideneoxazolidine-2-one (17.5 g, 49.6 mmol), which was dissolved in isopropyl ether (40 mL). Then, conc. HCl (15 mL) was added and the mixture was heated under reflux for 3 h until all of the precipitating hydrochloride of the imino form dissolved. After completion of the reaction, the reaction mixture was transferred into a separating funnel and the organic layer was separated by addition of water. The organic layer was dried with anhydrous magnesium sulfate and thereafter the desiccant was removed and the solvent was distilled off under vacuum. Hexane (15 mL) was added to the resulting crude product and, upon standing at room temperature, 3-(4-chloro-5-cyclopentyloxy-2-fluorophenyl)-5-isopropyliden-2,4-oxazolidinedione precipitated as a pale yellow crystal (13.28 g; yield, 79.3%), which was isolated by filtration.

MP: 104.5°–105.0° C.

$^1$H-NMR(CDCl$_3$, TMS, ppm): δ1.49–1.97(8H, m), 2.03(3H, s), 2.31(3H, s), 4.73(1H, m), 6.88(1H, d, J$_{HF}$=6.6 Hz), 7.33(1H, d, J$_{HF}$=8.5 Hz).

IR(KBr disk, cm$^{-1}$): 2970, 1815, 1740, 1500, 1200.

EXAMPLE 10

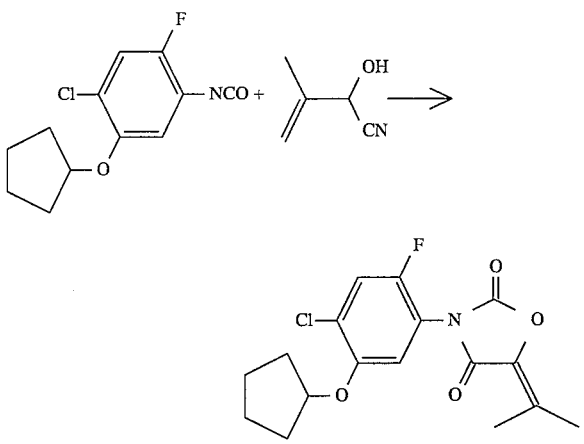

A round-bottomed flask (200 cc) was charged with 4-chloro-5-cyclopentyloxy-2-fluorophenyl isocyanate (2.07 g; 8.10 mmol) and triethylamine (0.5 mL), as well as isopropyl ether (20 mL) and methacrolein cyanohydrin (1.65 g, 17.0 mmol) was dropwise added slowly with stirring under cooling in an ice-water bath. After the addition, the mixture was heated to room temperature and, after further addition of triethylamine (0.5 mL), the mixture was stirred overnight as such. After confirming the production of an imino form by TLC, conc. HCl (10 mL) was added and the mixture was heated with stirring at 60° C. for 2 h until all of the precipitating hydrochloride of the imino form dissolved. After completion of the reaction, the reaction mixture was transferred into a separating funnel and washed successively with aqueous 1N sodium hydroxide and 1N HCl. The organic layer was dried with anhydrous magnesium sulfate and thereafter the desiccant was removed and the solvent was distilled off under vacuum. The resulting crude product was purified by silica gel column chromatography (eluting solvents: ethyl acetate/hexane=1/10) and then recrystallized from toluene/hexane to give 3-(4-chloro-5-cyclopentyloxy-2-fluorophenyl)-5-isopropyliden-2,4-oxazolidinedione as a white crystal (1.73 g; yield, 63.2%).

EXAMPLE 11

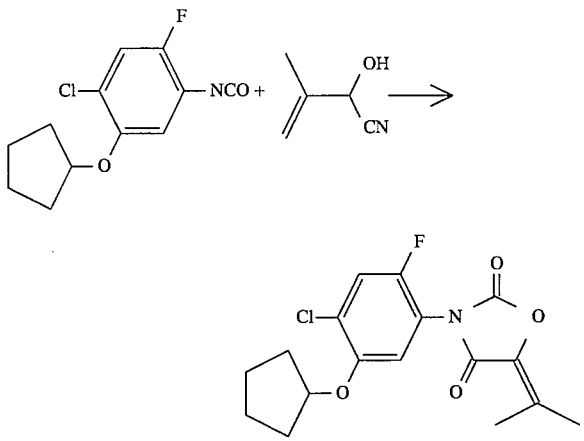

A round-bottomed flask (3000 cc) equipped with a mechanical stirrer was charged with 4-chloro-5-cyclopentyloxy-2-fluorophenyl isocyanate (215 g, 0.84 mol), triethylamine (5.4 mL) and solvent toluene (1000 mL) and methacrolein cyanohydrin (102 g, 1.05 mol) was dropwise added slowly with stirring at room temperature. After the addition, the mixture was heated to 40° C. and stirred for 2 h. Subsequently, conc. HCl (200 mL) was added to the stirred mixture, whereupon an imino form precipitated as a hydrochloride, which was heated as such up to 110° C. and stirred for 2.5 h. The reaction mixture was cooled to about 40° C. and thereafter aqueous 5N sodium hydroxide (325 mL) was added, followed by stirring at 50° C. for 2 h. After completion of the reaction, the organic layer was separated from the resulting mixture and the aqueous layer was subjected to extraction with toluene (200 mL×2). The organic layers were combined and washed successively with aqueous 1N sodium hydroxide (100 mL×2), 1N HCl (200 mL×2) and water (300 mL). The organic layers were dried with anhydrous magnesium sulfate and thereafter the desiccant was removed and the solvent was distilled off under vacuum. Hexane (ca. 300 mL) was added to the resulting brown oil and the mixture was left to stand at room temperature. The precipitating crystal was isolated by filtration and dried thoroughly to give 3-(4-chloro-5-cyclopentyloxy-2-fluorophenyl)-5-isopropyliden-2,4-oxazolidinedione as a white crystal (184 g; yield, 62.0%).

EXAMPLE 12

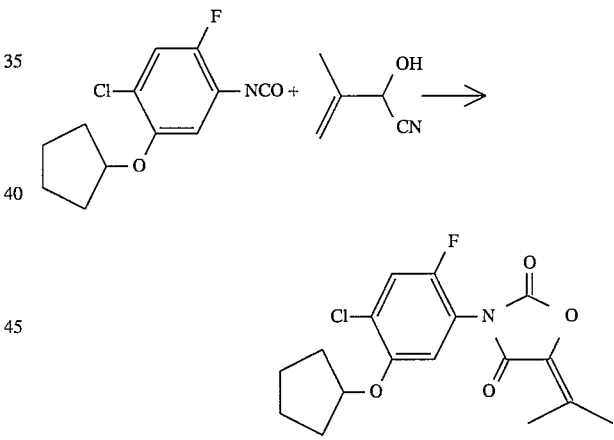

A round-bottomed flask (3000 cc) equipped with a mechanical stirrer was charged with 4-chloro-5-cyclopentyloxy-2-fluorophenyl isocyanate (206 g, 0.81 mol), triethylamine (4.0 mL) and solvent toluene (900 mL) and methacrolein cyanohydrin (97.8 g, 1.01 mol) was dropwise added slowly with stirring at room temperature. After the addition, the mixture was heated to 40° C. and stirred for 1 h. Subsequently, conc. HCl (200 mL) was added to the stirred mixture, whereupon an imino form precipitated as a hydrochloride, which was heated as such up to 110° C. and stirred for 2 h. The reaction mixture was cooled to about 40° C. and thereafter aqueous 5N sodium hydroxide (250 mL) was added, followed by stirring at 50° C. for 2 h. After completion of the reaction, the organic layer was separated from the resulting mixture and the aqueous layer was subjected to extraction with toluene (50 mL×3). The organic layers were combined and washed successively with aqueous 1N sodium hydroxide (1250 mL×4), 1N HCl (200 mL) and water (200 mL×2). The organic layers were dried with anhydrous magnesium sulfate and thereafter the desiccant was removed and the solvent was distilled off under vacuum. A brown oil resulted to which preliminarily prepared acidic methanol {MeOH (1400 mL/6 N HCl (5 mL)} was added and the mixture was heated to form a homogeneous solution; thereafter, 6N HCl (60 mL) was further added and the mixture was left to stand so that it slowly cooled to room temperature. The precipitating crystal was isolated by filtration and dried thoroughly to give 3-(4-chloro-5-cyclopentyloxy-2-fluorophenyl)-5-isopropyliden-2,4-oxazolidinedione as a white crystal (216 g; yield, 75.7%).

EXAMPLE 13

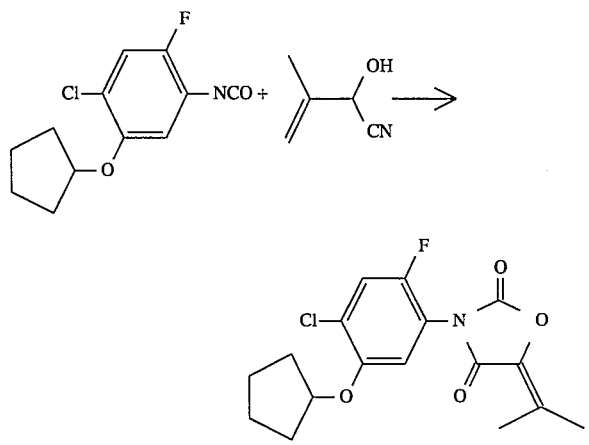

A round-bottomed flask (200 cc) was charged with 4-chloro-5-cyclopentyloxy-2-fluorophenyl isocyanate (25.6 g, 0.10 ml), methacrolein cyanohydrin (10.5 g, 0.10 mol) and solvent toluene (70 mL) and triethylamine (0.10 g) was subsequently added at room temperature, followed by stirring at 80° C. for 3 h. The reaction mixture was cooled to room temperature and 17% HCl (80 mL) was added, whereupon an imino form precipitated as a hydrochloride, which was heated as such and stirred under reflux for 2 h. After completion of the reaction, the organic layer was separated from the resulting mixture and the aqueous layer was subjected to extraction with toluene (20 mL×2). The organic layers were combined and washed successively with aqueous 1N sodium hydroxide and 1N HCl. The organic layers were dried with anhydrous magnesium sulfate and thereafter the desiccant was removed and the solvent was distilled off under vacuum. A brown oil resulted, to which hexane (30 mL) was added and the mixture was left to stand at room temperature. The precipitating crystal was isolated by filtration and dried thoroughly to give 3-(4-chloro-5-cyclopentyloxy-2-fluorophenyl)-5-isopropyliden-2,4-oxazolidinedione as a white crystal (17.5 g; yield, 49.4%).

Reference Example 1

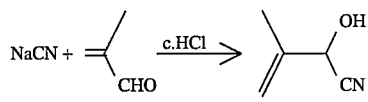

A two-necked round-bottomed flask (3000 cc) was charged sodium cyanide (52.4 g, 1.07 mol) and diisopropyl ether (500 mL), and methacrolein (70.1 g, 1.00 mol) was added under cooling in an ice-water bath. Then, the mixture was stirred under cooling while conc. HCl (89 mL) was dropwise added, at an insufficient rate for gases to evolve. After the addition, the mixture was heated to room temperature and stirred for an additional 1 h. After completion of the reaction (2 h later), the supernatant was transferred into a separating funnel, washed with a saturated solution of sodium hydrogensulfite (10 mL×3) and dried with anhydrous magnesium sulfate. After removing the desiccant, the solvent was distilled off under vacuum to give a colorless clear solution of methacrolein cyanohydrin (92.5 g; yield, 95.2%).

BP: 86°–87° C./8 mmHg $^1$H-NMR(400 MHz, CDCl$_3$, TMS, ppm): δ1.91(3H, s), 3.25(1H, br s), 4.88(1H, s), 5.14(1H, m), 5.33(1H, m).

IR(neat, cm$^{-1}$): 3450, 2950, 2275, 1660, 1450, 1390, 1090, 1060, 920

Reference Example 2

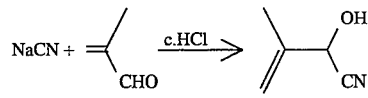

A two-necked round-bottomed flask (200 cc) was charged sodium cyanide (2.50 g, 51.0 mmol) and diethyl ether (30 mL), and methacrolein (3.00 g, 42.8 mmol) was added under cooling in an ice-water bath. Then, stirred conc. HCl (2.9 mL) was dropwise added slowly over 15 min under cooling. After the addition, the mixture was heated to room temperature and stirred for an additional 1 h. After completion of the reaction, the supernatant was transferred into a separating funnel, washed with a saturated solution of sodium hydrogensulfite (5 mL×2) and dried with anhydrous magnesium sulfate. After removing the desiccant, the solvent was distilled off under vacuum to give a colorless clear solution of methacrolein cyanohydrin (3.27 g; yield, 78.7%).

The thus obtained compounds of the present invention have superior herbicidal performance as already described herein. The compounds of the invention may be used as herbicides on their own but more often than not they are mixed with one or more adjuvants for use as herbicides. Common adjuvants include various carriers, diluents, solvents, surfactants, stabilizers, etc., which are incorporated and preferably formulated in suitable forms such as a wettable powder, emulsifiable concentrate, dust, granules and a flowable by usual methods.

One of the adjuvants in the herbicides that contain the compounds of the invention as an active ingredient is a solvent, suitable examples of which include alcohols, ketones, ethers, aliphatic or aromatic hydrocarbons, halogenated hydrocarbons, acid amides, esters, nitriles, etc.; these are used either alone or in admixture of two or more kinds.

Exemplary diluents that can be used include mineral powders including clays such as kaolin and bentonite, talcs such as talc and pyrophyllite and oxides such as diatomaceous earth and white carbon, as well as plant powders such as soybean meals and CMC. If desired, surfactants may be used as spreaders, dispersants, emulsifiers and penetrants. The surfactants may comprise nonionic surfactants, cationic surfactants, amphoteric surfactants, etc. These surfactants may be used either alone or in admixture of two or more kids depending on the application.

Preferred methods of using herbicides containing the compounds of the invention as an active ingredient include a soil treatment, a water-surface treatment and a foliage treatment and particularly good results can be achieved by application before the weeds to be controlled germinate and up to the time when their seedlings emerge.

The herbicides containing the compounds of the invention as an active ingredient may be used in either admixture or combination with other active components that will not interfere with the herbicidal activity of the active ingredient of interest, such as other herbicides, insecticides, fungicides, plant growth regulators, etc.

The present invention will now be described in greater detail with reference to exemplary herbicidal formulations containing compounds of the invention as an active ingredient, as well as to the results of the review of the herbicidal effect of the herbicide of interest. In the following description, all "parts" are by weight.

Formulation Example 1 (Emulsifiable Concentrate)

A compound of the invention (20 parts), xylene (35 parts), cyclohexanone (40 parts) and Sorpol 900A (5 parts; Toho Chemical Industry) were mixed uniformly to prepare an emulsifiable concentrate.

Formulation Example 2 (Wettable Powder)

A mixture consisting of a compound of the invention (50 parts), diatomaceous earth (25 parts), clay (22 parts) and Lunox R100C (3 parts; Toho Chemical Industry) was evenly blended and ground to prepare a wettable powder.

Formulation Example 3 (Granules)

A mixture consisting of a compound of the invention (5 parts), bentonire (35 parts), talc (55 parts) and sodium lingosulfonate (5 parts) was evenly blended and ground, followed by kneading in the presence of added water and extrusion through a granulator to produce granules, which were subsequently dried and screening to yield the finished granules.

Using the formulations prepared by the above described methods, the herbicidal effects of compounds of the present invention were investigated in accordance with the methods described in the Test Examples that are set forth below, and the results are shown in Tables 2–4. The growth inhibition of the plants under test was evaluated by the criteria set forth in Table 1.

TABLE 1

| Criteria for Evaluation | |
|---|---|
| Growth | Inhibition |
| 1 | 0% |
| 2 | 25% |
| 3 | 50% |
| 4 | 75% |
| 5 | 100% |

The compound used as a reference for comparison was commercial Chlorphthalim (A) set forth below and it was formulated as herbicidal preparations and applied for treatments in the same manner as the compounds of the invention and its herbicidal activity and crop injury were investigated by the same criteria for evaluation:

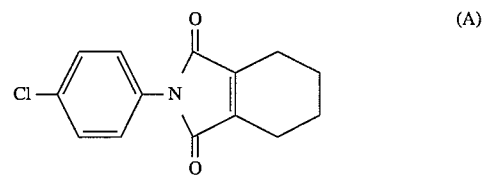

(A)

Test Example 1 (Effect on Weeds in Ricefields)

Pots of 1/5,000 were filled with the soil of ricefields, which was sown with the seeds of *Echinochloa oryzicola, Monochoria vaginalis, Scirpus juncoides, Eleocharis acicularis* and other annual broadleaf weeds and transplanted with rice (variety: koshihikari) seedlings in the 2- or 3-leaf stage and thereafter kept submerged with water. One day later, the wettable powders or emulsifiable concentrates of compounds of the invention that were prepared in accordance with the Formulation Examples were diluted and dripped to give specified doses per are. On the 15th day after the treatment, the herbicidal effect on the plants under test and the injury to the rice plant were investigated in accordance with the criteria for evaluation set forth in Table 1 and the results were as shown in Table 2.

TABLE 2

Effect of Pre-Emergence Soil Treatment in Ricefields

| Comp. No. | Dose applied g/a | Echinochloa oryzicola | Cyperus difformis | Other annual broadleaf weeds | Monochoria vaginalis | Scirpus juncoides | Eleocharis acicularis | Crop injury Rice |
|---|---|---|---|---|---|---|---|---|
| 1 | 2.5 | 4.5 | 5 | 5 | 5 | 4.2 | 5 | 1.2 |
|   | 1.0 | 4 | 5 | 5 | 5 | 4 | 5 | 1.1 |
| 2 | 2.5 | 5 | 5 | 5 | 5 | 4.5 | 5 | 1.3 |
|   | 1.0 | 4.8 | 5 | 5 | 5 | 4 | 4 | 1.2 |
|   | 0.5 | 3.5 | 4 | 4 | 4 | 3 | 3 | 1.1 |
| 5 | 2.5 | 5 | 5 | 5 | 5 | 5 | 5 | 1.2 |
|   | 1.0 | 4.9 | 5 | 5 | 5 | 5 | 5 | 1.1 |
| A | 2.5 | 5 | 5 | 5 | 5 | 5 | — | 5 |
|   | 1.0 | 5 | 5 | 5 | 5 | 4.8 | — | 3 |
|   | 0.5 | 3 | 5 | 4.8 | 5 | 4.5 | — | 1.5 |

Test Example 2 (Effect by Soil Treatment in Non-Ricefields)

Vats each having an area of 10×10 cm² and a depth of 5 cm were filled with the soil of non-ricefields, which was sown with *Echinochloa crusgalli, Digitalia ciliaris, Amaranthus viridis, Chenopodium album* and corn, with the seeds being then covered with a soil layer 0.5 cm thick. On the next day, the wettable powders or emulsifiable concentrates of compounds of the invention that were prepared in accordance with the Formulation Examples were diluted and applied over the covering soil layer uniformly to give specified doses per are. On the 15th day after the treatment, the herbicidal effect on the weeds under text and the injury to the corn were investigated in accordance with the criteria for evaluation set forth in Table 1 and the results were as shown in Table 3.

per are. On the 10th day after the treatment, the herbicidal effect on the weeds under test was investigated by the criteria for evaluation set forth in Table 1 and the results were as shown in Table 4.

TABLE 3

Effect in the Treatment of Soil of Non-Ricefields

| Comp. No. | Dose applied g/a | Echinochloa crusgalli | Digitalia ciliaris | Amaranthus viridis | Chenopodium album | Crop injury Corn |
|---|---|---|---|---|---|---|
| 1 | 10.0 | 1.5 | 1.8 | 3 | 2.5 | 1 |
|   | 5.0 | 1.2 | 1.5 | 2 | 2 | 1 |
| 2 | 10.0 | 1.5 | 2 | 3 | 2 | 1.2 |
|   | 5.0 | 1.2 | 1.5 | 1.5 | 1.5 | 1 |
| 5 | 10.0 | 3 | 4.5 | 5 | 5 | 1.2 |
|   | 5.0 | 2.5 | 3 | 4.6 | 4.9 | 1 |
| A | 10.0 | 2.5 | 2.5 | 3 | 4 | 1.2 |
|   | 5.0 | 2 | 2 | 3 | 3 | 1.2 |

Test Example 3 (Effect by Foliage Treatment)

Vats each having an area of 10×10 cm² and a depth of 5 cm were filled with the soil of non-ricefields, which was sown with *Echinochloa crusgalli, Abutilon theophrasti, Amaranthus viridis* and *Chenopodium album*. Fifteen days later, the wettable powders or emulsifiable concentrates of compounds of the invention that were prepared in accordance with the Formulation Examples were diluted, adjusted to specified concentrations and thereafter sprayed to the stems and leaves of the grown plants using 20 liters of water

TABLE 4

Effect in Foliage Treatment

| Comp. No. | Dose applied ppm | Herbicidal Effect | | | |
|---|---|---|---|---|---|
| | | Echinochloa crusgalli | Abutilon theophrasti | Amaranthus viridis | Chenopodium album |
| 1 | 500 | 4 | 5 | 5 | 4.8 |
| | 100 | 2.8 | 5 | 5 | 4 |
| 2 | 500 | 2 | 5 | 5 | 4.2 |
| | 100 | 1.5 | 4.5 | 2.5 | 3.2 |
| 3 | 500 | 1.5 | 5 | 1.8 | 2.5 |
| | 100 | 1.2 | 2.5 | 1.3 | 2 |
| 5 | 500 | 4.5 | 5 | 5 | 5 |
| | 100 | 3 | 5 | 5 | 4.5 |
| A | 500 | 3.5 | — | 3.5 | 5 |
| | 100 | 2.5 | — | 2.5 | 2.5 |

Industrial Applicability

The compounds of the present invention have potent herbicidal activity on their own; what is more, by hydrolyzing them, oxazolidinedione derivatives which are useful as an active ingredient in herbicides can be manufactured in an industrially more advantageous manner and applications that exploit their features are also feasible.

We claim:

1. 4-Imino-oxazolidine-2-one derivatives represented by the general formula (1):

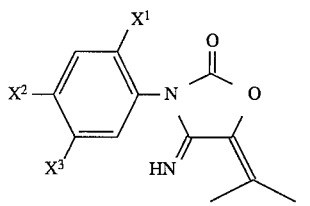

(where $X^1$ is a hydrogen atom or a halogen atom; $X^2$ is a hydrogen atom, a halogen atom or an alkyloxy group; $X^3$ is a hydrogen atom, a halogen atom, an alkyloxy group, a cycloalkyloxy group or an alkynyloxy group) and salts thereof.

2. 4-Imino-oxazolidine-2-one derivatives according to claim 1, wherein $X^1$ is a hydrogen atom or a halogen atom, $X^2$ is a hydrogen atom, a halogen atom or an alkyloxy group having 1–6 carbon atoms, $X^3$ is a hydrogen atom, a halogen atom, an alkyloxy group having 1–6 carbon atoms, a cycloalkyloxy group having 3–6 carbon atoms or an alkynyloxy group having 3–4 carbon atoms, and salts thereof.

3. 4-Imino-oxazolidine-2-one derivatives according to claim 1, wherein $X^2$ is a hydrogen atom, a fluorine atom, a chlorine atom, a bromine atom, a methoxy group, an ethoxy group, a propoxy group, an isopropoxy group, a butoxy group, an isobutoxy group, a pentyloxy group or a hexyloxy group, and salts thereof.

4. 4-Imino-oxazolidine-2-one derivatives according to claim 1, wherein $X^3$ is a hydrogen atom, a fluorine atom, a chlorine atom, a bromine atom, a methoxy group, an ethoxy group, a propoxy group, an isopropoxy group, a butoxy group, an isobutoxy group, a pentyloxy group, a hexyloxy group, a cyclopropyloxy group, a cyclopentyloxy group, a cyclohexyloxy group, a propargyloxy group, a 1-butyn-3-yloxy group or a 2-butynyloxy group, and salts thereof.

5. 4-Imino-oxazolidine-2-one derivatives according to claim 2, wherein $X^1$ is a hydrogen atom, a fluorine atom, a chlorine atom or a bromine atom, $X^2$ is a hydrogen atom, a fluorine atom, a chlorine atom, a bromine atom, a methoxy group, an ethoxy group, a propoxy group, an isopropoxy group, a butoxy group, an isobutoxy group, a pentyloxy group or a hexyloxy group, $X^3$ is a hydrogen atom, a fluorine atom, a chlorine atom, a bromine atom, a methoxy group, an ethoxy group, a propoxy group, an isopropoxy group, a butoxy group, an isobutoxy group, a pentyloxy group, a hexyloxy group, a cyclopropyloxy group, a cyclopentyloxy group, a cyclohexyloxy group, a propargyloxy group, a 1-butyn-3-yloxy group or a 2-butynyloxy group, and salts thereof.

6. 4-Imino-oxazolidine-2-one derivatives according to claim 5, wherein $X^1$ is a hydrogen atom, a fluorine atom or a chlorine atom, $X^2$ is a chlorine atom or a methoxy group, and $X^3$ is a hydrogen atom, a chlorine atom, an isopropyloxy group, a cyclopentyloxy group or a 2-butynyloxy group, and salts thereof.

7. 4-Imino-oxazolidine-2-one derivatives according to claim 6, which are selected from the group consisting of compounds represented by the following formulas:

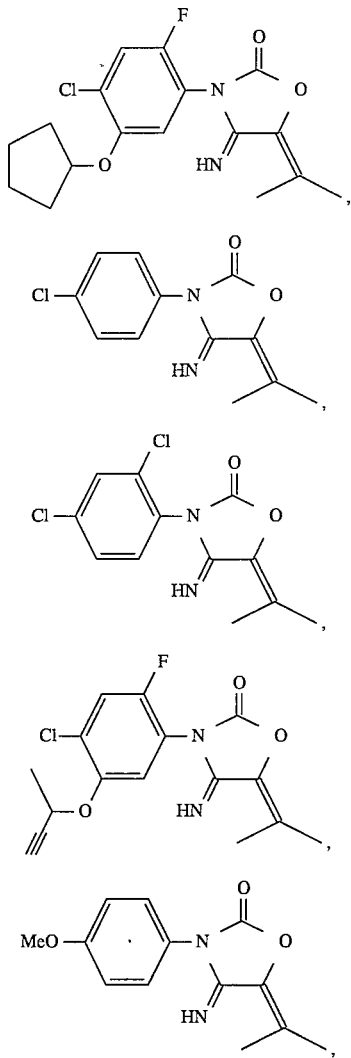

-continued

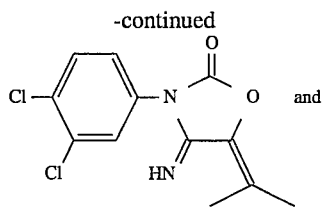

and

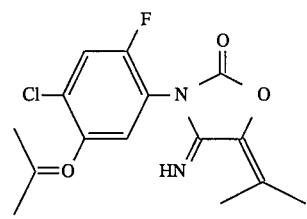

and salts thereof.

8. A process for producing a 4-imino-oxazolidine-2-one derivative represented by the general formula (1):

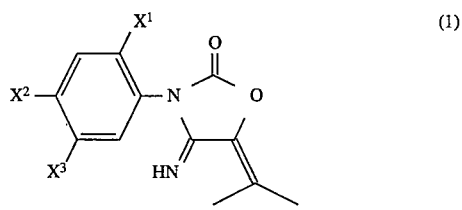

(where $X^1$ is a hydrogen atom or a halogen atom; $X^2$ is a hydrogen atom, a halogen atom or an alkyloxy group having 1–6 carbon atoms, $X^3$ is a hydrogen atom, a halogen atom, an alkyloxy group having 1–6 carbon atoms, a cycloalkyloxy group having 3–6 carbon atoms or an alkynyloxy group having 3–4 carbon atoms), characterized in that an aryl isocyanate represented by the general formula (2):

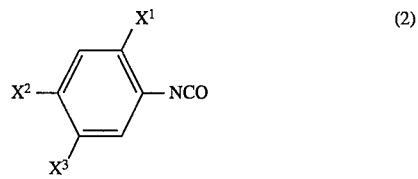

(where $X^1$ is a hydrogen atom or a halogen atom; $X^2$ is a hydrogen atom, a halogen atom or an alkyloxy group having 1–6 carbon atoms; $X^3$ is a hydrogen atom, a halogen atom, an alkyloxy group having 1–6 carbon atoms, a cycloalkyloxy group having 3–6 carbon atoms or an alkynyloxy group having 3–4 carbon atoms) is reacted with 1-cyano-2-methyl-2-propen-1-ol.

9. A herbicide containing as an active ingredient 4-imino-oxazolidine-2-one derivatives represented by the general formula (1):

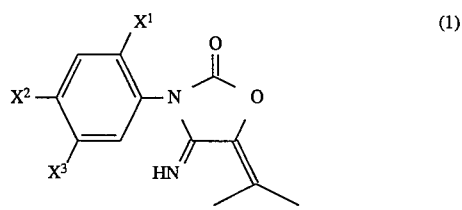

(where $X^1$ is a hydrogen atom or a halogen atom; $X^2$ is a hydrogen atom, a halogen atom or an alkyloxy group having 1–6 carbon atoms; $X^3$ is a hydrogen atom, a halogen atom, an alkyloxy group having 1–6 carbon atoms, a cycloalkyloxy group having 3–6 carbon atoms or an alkynyloxy group having 3–4 carbon atoms, and salts thereof.

10. A process for producing a 5-isopropyliden-2,4-oxazolidinedione derivative represented by the general formula (3):

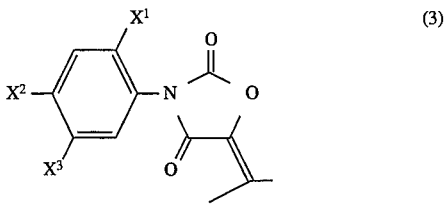

(where $X^1$ is a hydrogen atom or a halogen atom; $X^2$ is a hydrogen atom, a halogen atom or an alkyloxy group having 1–6 carbon atoms; $X^3$ is a hydrogen atom, a halogen atom, an alkyloxy group having 1–6 carbon atoms, a cycloalkyloxy group having 3–6 carbon atoms or an alkynyloxy group having 3–4 carbon atoms, characterized in that a 4-imino-oxazolidine-2-one derivative represented by the general formula (1):

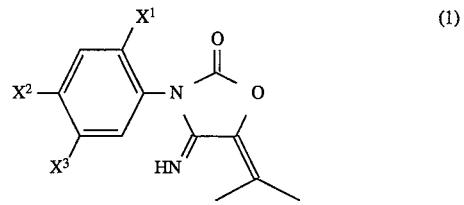

(where $X^1$ is a hydrogen atom or a halogen atom; $X^2$ is a hydrogen atom, a halogen atom or an alkyloxy group having 1–6 carbon atoms; $X^3$ is a hydrogen atom, a halogen atom, an alkyloxy group having 1–6 carbon atoms, a cycloalkyloxy group having 3–6 carbon atoms or an alkynyloxy group having 3–4 carbon atoms) is hydrolyzed under acidic conditions.

11. A process for producing a 5-isopropyliden-2,4-oxazolidinedione derivative represented by the general formula (3):

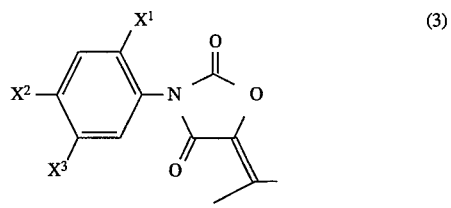

(where $X^1$ is a hydrogen atom or a halogen atom; $X^2$ is a hydrogen atom, a halogen atom or an alkyloxy group having 1–6 carbon atoms; $X^3$ is a hydrogen atom, a halogen atom, an alkyloxy group having 1–6 carbon atoms, a cycloalkyloxy group having 3–6 carbon atoms or an alkynyloxy group having 3–4 carbon atoms), characterized in that an aryl isocyanate represented by the general formula (2):

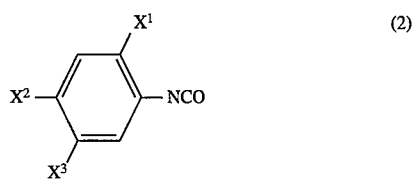

(where $X^1$ is a hydrogen atom or a halogen atom; $X^2$ is a hydrogen atom, a halogen atom or an alkyloxy group having 1–6 carbon atoms; $X^3$ is a hydrogen atom, a halogen atom, an alkyloxy group having 1–6 carbon atoms, a cycloalkyloxy group having 3–6 carbon atoms or an alkynyloxy group having 3–4 carbon atoms) is reacted with 1-cyano-2-methyl-2-propen-1-ol in the presence of a base and then hydrolyzing the imino group under acidic conditions.

\* \* \* \* \*